Figure 1:
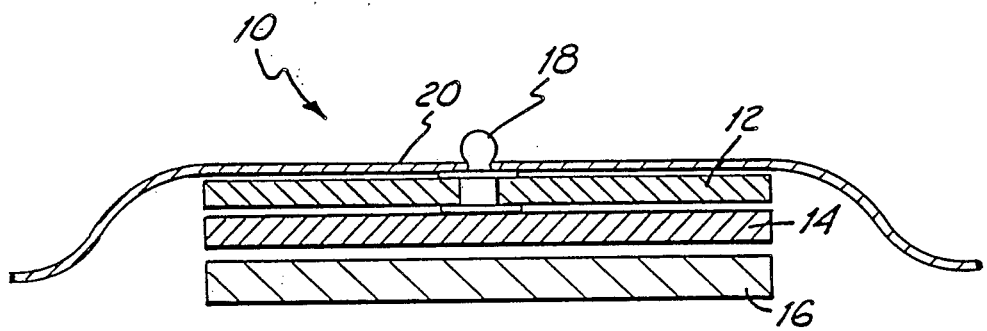

United States Patent [19]

Johnson et al.

[11] Patent Number: 4,973,303
[45] Date of Patent: Nov. 27, 1990

[54] PH BUFFERED ELECTRODE FOR MEDICAL IONTOPHORESIS

[75] Inventors: Michael T. V. Johnson, Minneapolis; Nina H. Lee, Richfield, both of Minn.

[73] Assignee: Empi, Inc., St. Paul, Minn.

[21] Appl. No.: 402,880

[22] Filed: Sep. 5, 1989

[51] Int. Cl.$^5$ .............................................. A61N 1/30
[52] U.S. Cl. ................................................... 604/020
[58] Field of Search .................. 604/20; 128/798, 802, 128/803

[56] References Cited

U.S. PATENT DOCUMENTS

| | | | |
|---|---|---|---|
| 4,166,457 | 9/1979 | Jacobsen et al. | 128/639 |
| 4,250,878 | 2/1982 | Jacobsen et al. | 128/635 |
| 4,416,274 | 11/1983 | Jacobsen et al. | 604/20 |
| 4,419,092 | 12/1983 | Jacobsen et al. | 604/20 |
| 4,474,570 | 10/1984 | Ariura et al. | 604/20 |
| 4,717,378 | 1/1988 | Perrault | 604/20 |
| 4,722,726 | 2/1988 | Sanderson et al. | 604/20 |
| 4,731,049 | 3/1988 | Parsi | 604/20 |
| 4,744,787 | 5/1988 | Phipps et al. | 128/798 X |
| 4,747,819 | 5/1988 | Phipps | 604/20 |
| 4,752,285 | 6/1988 | Petelenz et al. | 604/20 |
| 4,842,577 | 6/1989 | Konno et al. | 604/20 |

Primary Examiner—Lee S. Cohen
Attorney, Agent, or Firm—Kinney & Lange

[57] ABSTRACT

A pH buffered electrode for receiving electrical energy and producing an electric field. The pH buffered electrode includes a first conductive layer and a pH buffer layer adjacent the first conductive layer. The pH buffer layer includes a pH buffer covalently coupled to an immobilizing material such as resin beads or polymers. The immobilizing material renders the pH buffer immobile in the presence of an electric field and allows $H^+$ and $OH^-$ ions to be scavenged.

37 Claims, 1 Drawing Sheet

PH BUFFERED ELECTRODE FOR MEDICAL IONTOPHORESIS

BACKGROUND OF THE INVENTION

1. Field of the Invention.

The present invention relates generally to electrodes. In particular, the present invention relates to a pH buffered electrode for use in medical iontophoresis.

2. Description of the Prior Art.

The technique of iontophoresis employs an electric field to mobilize ionic medicaments through the skin. This therapeutic modality allows for the introduction of substances into the tissues and blood stream of a patient without the necessity of hypodermic injection and its concomitant untoward effects, such as pain and risk of infection. Delivery of drugs via iontophoresis also presents the advantage of avoiding first-pass metabolism of a medicament. When a medicament is taken orally and absorbed from the digestive tract into the blood stream, the blood containing the medicament first percolates through the liver, a metabolically active organ, before entering the general circulation for delivery to the target tissue. Thus much of the orally ingested medicament may be metabolically inactivated before it has a chance to exert its pharmacologic effect. Local delivery of medicaments, therefore, presents advantages over hypodermic injection, an invasive, inconvenient, and sometimes risky technique, and oral administration, a modality characterized by inefficiency and unpredictability.

The usefulness of electrodes in medical procedures is limited, however, by a finite incidence of skin burns resulting from the passage of current through the skin. The primary causative factor of this skin burning is an electrochemical mechanism whereby the applied current causes electrolysis of water and generates either $H^+$ or $OH^-$ ions, which cause pH changes that ultimately lead to a burning of the skin under the electrode. For example, in an iontophoresis procedure to mobilize a positively charged medicament through the skin, an aqueous reservoir containing the positively charged medicament will be placed at the anode, or positive electrode. A negatively charged electrode or cathode, will act as an indifferent electrode. When current is applied to the iontophoresis system, the medicament will be driven toward and through the skin, but the application of the current at the positive electrode will also cause the following reaction:

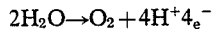

The $H^+$ ions will move rapidly to the skin, decrease the pH of the aqueous environment to dangerous levels, and ultimately cause a burning of the skin. At the cathode, in this example the indifferent electrode, the following reaction occurs:

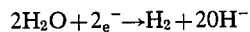

The $OH^-$ ions move rapidly to the skin, increase the pH of the aqueous environment at the electrode to dangerous levels, and ultimately cause a burning of the skin under the negative electrode. In an iontophoresis procedure to mobilize a negatively charged medicament through the skin, the same reactions will occur at the anode and cathode, with the cathode impregnated with medicament ions and the anode acting as the indifferent electrode. In a typical application of current through electrodes contacting the skin, the pH under the anode decreases to less than 1.5 (acidic), and the pH under the cathode increases to exceed 10 (basic). Application of current in an iontophoresis procedure, then, not only mobilizes the ionic medicament across the skin, but also causes the electrolysis of water and the generation of reactive $H^+$ and $OH^-$ ions that cause a burning of the skin. In addition, a substantial amount of current is wasted in driving the $H^+$ and $OH^-$ ions and the presence of these ionic species in the iontophoretic system aggravates the problem of quantification of the amount of medicament delivered during the iontophoretic procedure.

A substantial effort has been directed toward alleviating the problem associated with electrochemical burns in iontophoresis. One approach has been to introduce a buffer into the iontophoretic system. A buffer renders a solution more resistant to a change in pH following addition of acid ($H^+$) or base ($OH^-$) than does an equal volume of water. In this approach, a soluble buffer salt is included in the solution containing medicament ions. The buffer will be a weak acid or base that has been titrated with a strong base or strong acid to form a salt of the weak acid or weak base capable of scavenging $H^+$ or $OH^-$ ions. In scavenging the undesirable $H^+$ or $OH^-$ ions, the buffer will reduce the incidence of skin burns under the iontophoresis electrode.

This use of a buffer in an iontophoresis system, however, presents several problems. Firstly, buffer ion molecules and their complementary ions tend to be smaller and thus more mobile than medicament ions. When current is applied to an iontophoretic system containing a buffer, the buffer ions will move more rapidly toward and through the skin than the medicament ions. Thus, current is consumed in driving buffer ions across the skin instead of desirable medicament ions, and it is more difficult to quantify the amount of medicament driven through the skin. Although a buffer incorporated into an iontophoresis system could successfully scavenge undesirable $H^+$ and $OH^-$ ions and reduce burning of the skin, the problems associated with mobile buffer ions overcome any advantage this approach might have. (Problems of this type are described in the Background section of U.S. Pat. No. 4,752,285.) Other methods and approaches to the electrochemical burn problem include maintaining the voltage at the interface of the electrode and the medicament solution below the electrolysis voltage of water (e.g. U.S. Pat. No. 4,752,285) or the use of a sacrificial electrode to minimize the production of unwanted species (e.g. U.S. Pat. No. 4,744,787). A continuing effort is under way to effectively alleviate the electrochemical burn problem associated with medical iontophoresis.

SUMMARY OF THE INVENTION

The present invention is a pH buffered electrode for receiving electrical energy and producing an electric field. The electrode includes a conductive layer and a pH buffer layer adjacent the conductive layer, with the pH buffer layer comprised of a pH buffer coupled to an immobilizing material. The immobilizing material effectively renders the buffer immobile in the presence of an electric field while allowing the undesirable $H^+$ and $OH^-$ ions to be scavenged and preventing electrochemical burning of the skin. The inventive electrode can be used in medical iontophoresis to drive medicament ions across the skin. The buffer remains immobilized during the iontophoresis procedure, obviating the heretofore intractable problem associated with the presence of buffers in iontophoresis systems.

In one embodiment, the conductive layer is fabricated from metal, carbon rubber, or a conductive polymer, and is covered with an electrically nonconductive adhesive material. The immobilizing material of the buffer layer can be either resin beads or polymers, to which buffer molecules are covalently attached. Weak acids or weak bases, preferably organic in nature, are coupled to the resin bead or polymer, and, having been titrated with strong base or strong acid, form buffer salts capable of scavenging undesirable H or $OH^-$ ions.

A second conductive layer can be located adjacent the pH buffer layer. The second conductive layer contains an aqueous reservoir of medicament ions and complementary ions. This electrode would be the active, or medicament-impregnated, electrode in a medical iontophoresis procedure. By virtue of their covalent attachment to the resin beads or polymers, the buffer molecules are immobile in the presence of an electric field. The buffer molecules will not move in response to the application of current and will not interfere with the efficient mobilization of medicament ions across the skin.

In another embodiment of the inventive electrode, the second conductive layer is a conductive polymer or a porous material containing an electrolyte solution. This electrode can operate as the indifferent electrode in a medical iontophoresis procedure. The buffer layer, adjacent the conductive layer, will scavenge undesirable + or $OH^-$ ions generated from the electrolysis of water, and safeguard the skin from electrochemical burns that would otherwise occur under the indifferent electrode.

BRIEF DESCRIPTION OF THE INVENTION

FIG. 1 is a sectional view of the pH buffered electrode of the present invention.

DETAILED DESCRIPTION OF THE PREFERRED EMBODIMENTS pH buffered electrode 10, shown in FIG. 1, includes a first conductive layer 12, a buffer layer 14, and a second conductive layer 16. Conductive layer 12 can be fabricated from metal, carbon rubber, or conductive polymer. A terminal 18 is fastened to the first conductive layer and functions to couple electrode 10 to an electrical power source such as a DC generator. Preferably, an adhesive electrode covering 20 is placed over conductive layer 12 to provide structural support to the electrode and adherence to the skin.

Buffer layer 14 includes an immobilizing material to which buffer molecules are covalently attached. Resin beads and polymers can be used as immobilizing material in buffer layer 14. Buffer layer 14 is positioned adjacent conductive layer 12, as shown in FIG. 1. Preferably, buffer layer 14 is formed by a layer of resin beads or polymers applied to the first conductive layer and laminated thereto. Here buffer layer 14 is situated at the interface between first conductive layer 12 and second conductive layer 16.

It should be noted that the immobilized pH buffer need not necessarily take the form of a layer at the interface between the first conductive layer 12 and the second conductive layer 16. Indeed, the resin beads or polymers, to which the buffer molecules are attached, could be included as an integral feature of second conductive layer 16.

If electrode 10 acts as the anode, or positively charged electrode, in an iontophoresis system, buffer layer 14 will include an immobilizing material such as resin beads or polymers to which weak acids are covalently attached. Weak acids, attached to resin beads or polymers, will have been titrated with a strong base prior to placement in electrode 10, to form buffer salts. At the anode, weak acids will scavenge + ions generated from the electrolysis of water resulting from the application of current to the iontophoresis system. The weak acids covalently attached to the resin beads or polymers can be organic in nature, and therefore can contain deprotonated carboxyl groups (COO.) available for scavenging + ions. An example of a commercially available resin bead to which a weak organic acid is attached is Amberlite.

If electrode 10 acts as the cathode, or negatively charged electrode, in an iontophoresis system, buffer layer 14 will include an immobilizing material, such a resin beads or polymers to which weak bases are covalently attached. Weak bases, attached to resin beads or polymers, will have been titrated with a strong base prior to placement in electrode 10, to form buffer salts. At the anode, weak acids will scavenge $H^+$ ions generated from the electrolysis of water resulting from the application of current to the iontophoresis system. The weak acids covalently attached to the resin beads or polymers can be organic in nature, and therefore can contain deprotonated carboxyl groups ($COO^-$) available for scavenging $H^+$ ions. An example of a commercially available resin bead to which a weak organic acid is attached is Amberlite.

If electrode 10 acts as the cathode, or negatively charged electrode, in an iontophoresis system, buffer layers 14 will include an immobilizing material, such a resin beads or polymers to which weak bases are covalently attached. Weak bases, attached covalently to resin beads or polymers, will have been titrated with a strong acid prior to placement in electrode 10, to form buffer salts. At the cathode, weak bases will scavenge $OH^-$ ions generated from electrolysis of water resulting from application of current to the iontophoresis system. The weak bases covalently attached to the resin beads or polymers can be organic in nature and therefore can contain protonated amide groups ($CONH_3^+$) available for scavenging of $OH^-$ ions. An example of a commercially available resin bead to which a weak organic base is attached is IRA-900.

Second conductive layer 16 can be positioned adjacent buffer layer 14, as seen in FIG. 1. In one embodiment of the present invention, the second conductive layer 16 is a conductive material impregnated with an aqueous medicament solution. The medicament solution will include solubilized medicament ions and complementary ions, such as chloride or sodium ions. This conductive material containing medicament would form the medicament reservoir of an active electrode in a medical iontophoresis procedure. When current is applied to the electrode 10 via an electrical power source coupled to electrode 10 through terminal 18, medicament ions would be mobilized from the reservoir through the skin. Buffer layer 14, containing immobilized buffer molecules, will scavenge + ions or $OH^-$ ions depending on whether the medicament-impregnated electrode operates as the anode or cathode.

In another embodiment of the present invention, second conductive layer 16 is a conductive polymer or a porous material containing an electrolyte solution. Here the electrode 10 will operate as the indifferent electrode in a medical iontophoresis procedure. When current is applied to an iontophoresis system, the buffer layer 14, containing immobile buffer molecules, will scavenge undesirable + or OH− ions generated from the electrolyses of water at the indifferent electrode, depending upon whether the indifferent electrode operates as the anode or the cathode.

Thus electrochemical burning of the skin is reduced or avoided at both the active and indifferent electrodes via the use of the inventive electrode. The problem associated with mobility of buffer molecules in the presence of an electric field, previously perceived as intractable, is obviated via the immobilization of the buffer molecules onto either resin beads or polymers. The reduction of electrochemical burning is achieved without the disadvantages associated with the presence of mobile buffer molecules in the iontophoresis system.

Although the present invention has been described with reference to preferred embodiments, workers skilled in the art will recognize that changes may be made in form and detail without departing from the spirit and scope of the invention.

For example, it should be recognized that the pH buffered electrode can also be used in conjunction with a TENS (transcutaneous electrical nerve stimulator) device in order to minimize electrochemical burning of the skin associated with a TENS procedure.

What is claimed is:

1. A pH buffered electrode for receiving electrical energy and producing an electric field, comprising:
   a first conductive layer;
   a pH buffer layer adjacent the first conductive layer and including:
      a pH buffer; and
      an immobilizing material for immobilizing the buffer in the presence of the electric field; and
   a second conductive layer adjacent the pH buffer layer and opposite the buffer layer from the first conductive layer.

2. The pH buffered electrode of claim 1, wherein the first conductive layer includes metal.

3. The pH buffered electrode of claim 1, wherein the first conductive layer includes carbon rubber.

4. The pH buffered electrode of claim 1, wherein the first conductive layer includes conductive polymer material.

5. The pH buffered electrode of claim 1, wherein the second conductive layer is a medicament reservoir containing an aqueous medicament solution of medicament ions and complementary ions.

6. The pH buffered electrode of claim 1, wherein the second conductive layer includes conductive polymer material.

7. The pH buffered electrode of claim 1, wherein the second conductive layer includes a porous material containing an electrolyte solution.

8. The pH buffered electrode of claim 1, and further comprising:
   an electrode covering positioned over the first conductive layer of the electrode and providing structural support and adherence to skin.

9. The pH buffered electrode of claim 8, wherein the electrode covering is an electrically nonconductive, adhesive material.

10. The pH buffered electrode of claim 1, and further comprising:
    a terminal for coupling with an electrical power source fastened to the first conductive layer.

11. The pH buffered electrode of claim 1, wherein the immobilizing material includes a resin bead.

12. The pH buffered electrode of claim 11, wherein the immobilized buffer is an acid coupled to the resin bead.

13. The pH buffered electrode of claim 11, wherein the immobilized buffer is a base coupled to the resin bead.

14. The pH buffered electrode of claim 11 and including $COO^-$ groups coupled to the resin bead.

15. The pH buffered electrode of claim 11 and including $NH_3^+$ groups coupled to the resin bead.

16. The pH buffered electrode of claim 1, wherein the immobilizing material is a polymer.

17. The pH buffered electrode of claim 16, wherein the immobilized buffer is a acid coupled to the polymer.

18. The pH buffered electrode of claim 16, wherein the immobilized buffer is a base coupled to the polymer.

19. The pH buffered electrode of claim 16, and including $COO^-$ groups coupled to the polymer.

20. The pH buffered electrode of claim 16, and including $NH_3^-$ groups coupled to the polymer.

21. A pH buffered electrode for medical iontophoresis, for receiving electrical energy and producing an electric field, comprising:
    a first conductive layer;
    a second conductive layer containing an aqueous medicament solution of medicament ions and complementary ions; and
    a pH buffer layer between the first conductive layer and the second conductive layer and including:
       a pH buffer; and
       an immobilizing material for immobilizing the buffer in the presence of the electric field.

22. The pH buffered electrode of claim 21, wherein the first conductive layer includes metal.

23. The pH buffered electrode of claim 21, wherein the first conductive layer includes carbon rubber.

24. The pH buffered electrode of claim 21, wherein the first conductive layer includes conductive polymer material.

25. The pH buffered electrode of claim 22, and further comprising:
    a terminal for coupling with an electrical power source fastened to the first conductive layer.

26. The pH buffered electrode of claim 21, wherein the immobilizing material is a resin bead.

27. The pH buffered electrode of claim 26, wherein the immobilized buffer is an acid coupled to the resin bead.

28. The pH buffered electrode of claim 26, wherein the immobilized buffer is a base coupled to the resin bead.

29. The pH buffered electrode of claim 26 and including $COO^-$ groups coupled to the resin bead.

30. The pH buffered electrode of claim 26 and including $NH_3^+$ groups coupled to the resin bead.

31. The pH buffered electrode of claim 21, wherein the immobilizing material is a polymer.

32. The pH buffered electrode of claim 31, wherein the immobilized buffer is a acid coupled to the polymer.

33. The pH buffered electrode of claim 31, wherein the immobilized buffer is a base coupled to the polymer.

34. The pH buffered electrode of claim 31, and including COO⁻ groups coupled to the polymer.

35. The pH buffered electrode of claim 31, and including NH$_3^+$ groups coupled to the polymer.

36. The pH buffered electrode of claim 21 and further including an electrically nonconductive adhesive covering extending over one or more of the layers to provide structural support and skin adhesion.

37. A pH buffered electrode for receiving electrical energy and producing an electric field, comprising:
   a first conductive layer;
   a second conductive layer; and
   a pH buffer layer between the first conductive layer and the second conductive layer, and including:
      a pH buffer; and
      an immobilizing material for immobilizing the buffer in the presence of the electric field.

* * * * *